(12) United States Patent
Wagner et al.

(10) Patent No.: US 9,239,294 B2
(45) Date of Patent: Jan. 19, 2016

(54) GEM IDENTIFICATION METHOD AND APPARATUS USING DIGITAL IMAGING VIEWER

(71) Applicant: GemEx Systems, Inc., Mequon, WI (US)

(72) Inventors: Randall Wagner, Mequon, WI (US); Kurt Schoeckert, Harford, WI (US); Xianghong Zhao, Mequon, WI (US)

(73) Assignee: Gemex Systems, Inc., Mequon, WI (US)

( * ) Notice: Subject to any disclaimer, the term of this patent is extended or adjusted under 35 U.S.C. 154(b) by 0 days.

(21) Appl. No.: 14/015,239

(22) Filed: Aug. 30, 2013

(65) Prior Publication Data

US 2014/0063292 A1 Mar. 6, 2014

Related U.S. Application Data

(63) Continuation-in-part of application No. 13/901,445, filed on May 23, 2013.

(60) Provisional application No. 61/695,746, filed on Aug. 31, 2012.

(51) Int. Cl.
| | |
|---|---|
| *G02B 27/02* | (2006.01) |
| *G01N 21/00* | (2006.01) |
| *G01N 21/87* | (2006.01) |
| *G02B 7/02* | (2006.01) |

(52) U.S. Cl.
CPC .............. *G01N 21/87* (2013.01); *G02B 7/026* (2013.01); *G02B 27/027* (2013.01); *G02B 27/028* (2013.01)

(58) Field of Classification Search
CPC .. G02B 25/002; G02B 27/025; G02B 27/027; G01N 21/87; G01N 21/8806; G01N 33/381

USPC .............. 359/802, 811, 818, 819; 356/30
See application file for complete search history.

(56) References Cited

U.S. PATENT DOCUMENTS

| | | | |
|---|---|---|---|
| 5,196,966 | A | 3/1993 | Yamashita |
| 6,731,439 | B1 | 5/2004 | Peachee |
| 6,980,283 | B1 | 12/2005 | Aggarwal |
| 7,468,786 | B2 | 12/2008 | Wagner et al. |
| 8,035,807 | B2 | 10/2011 | Wagner et al. |
| 2005/0190356 | A1 | 9/2005 | Sasian et al. |
| 2007/0109529 | A1 | 5/2007 | Wagner et al. |
| 2007/0280677 | A1 | 12/2007 | Drake et al. |
| 2009/0093274 | A1* | 4/2009 | Yamamoto ................... 455/566 |
| 2011/0009163 | A1 | 1/2011 | Fletcher et al. |

FOREIGN PATENT DOCUMENTS

| | | |
|---|---|---|
| WO | 2012032171 | 3/2012 |
| WO | 2012058641 | 5/2012 |

OTHER PUBLICATIONS

International Search Report for application PCT/US2013/042521, mailed Oct. 16, 2013.
International Search Report for application PCT/US2013/057619, mailed Feb. 7, 2014.

* cited by examiner

*Primary Examiner* — William Choi
(74) *Attorney, Agent, or Firm* — Nicholas A. Kees; Andrew C. Landsman; Godfrey & Kahn, S.C.

(57) ABSTRACT

A system and an apparatus for capturing a digital image of a particular gemstone from which specific and unique data can be extracted using digital image processing analysis, which data is used to positively identify a single gemstone from a database of gemstone images.

5 Claims, 11 Drawing Sheets

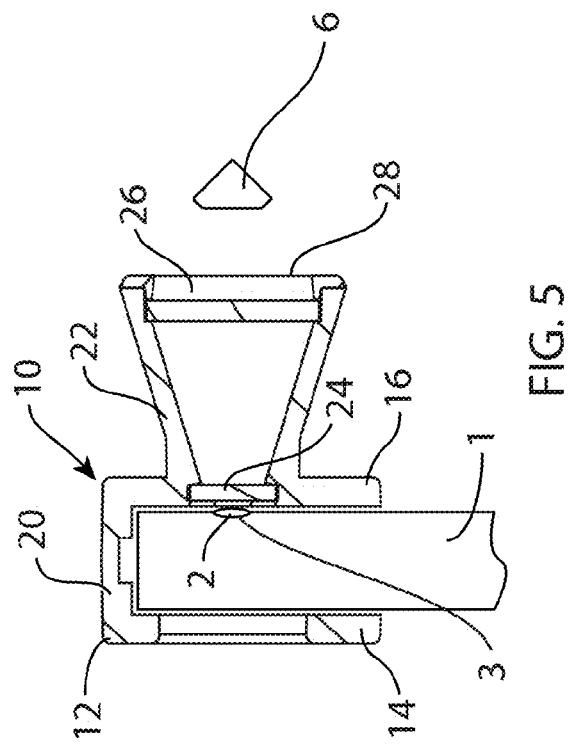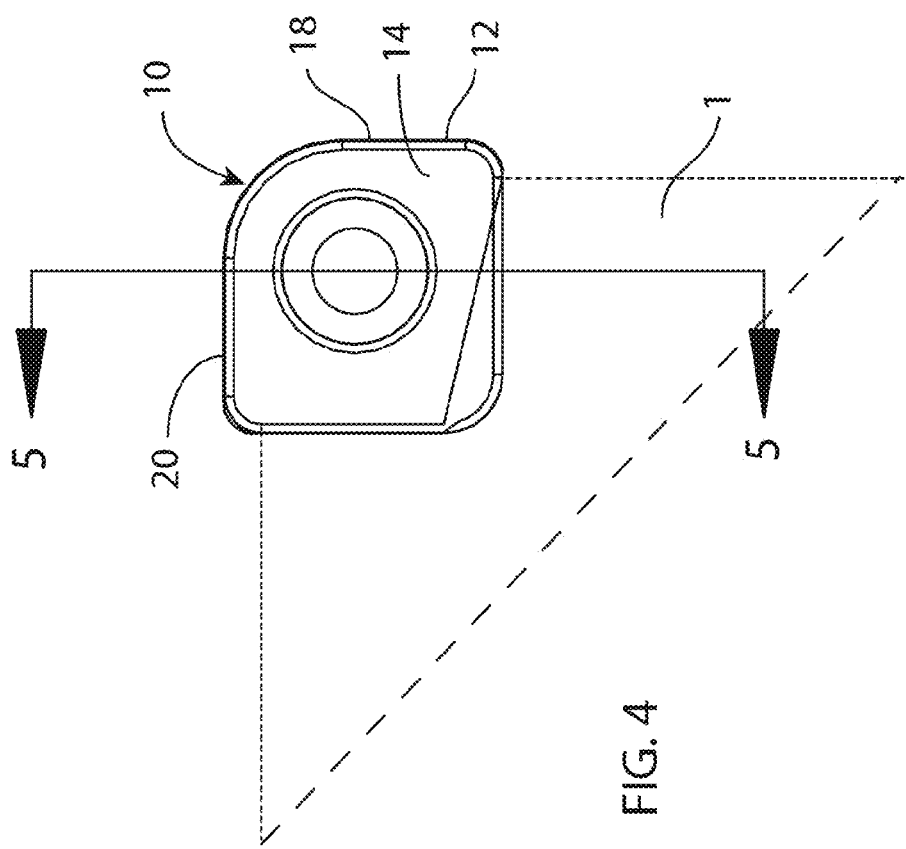

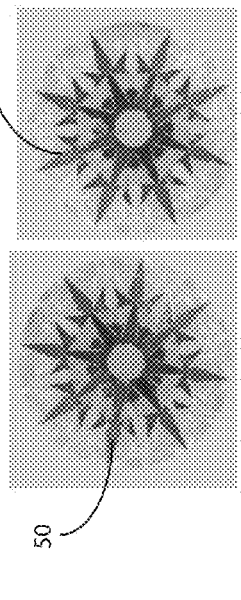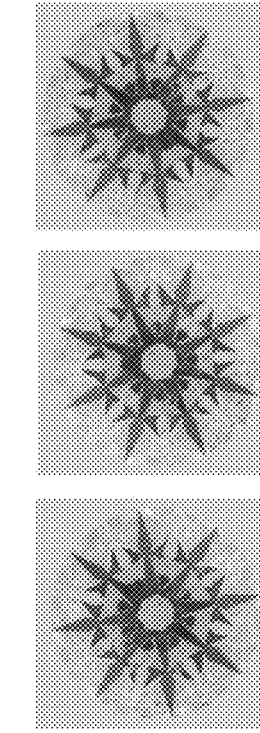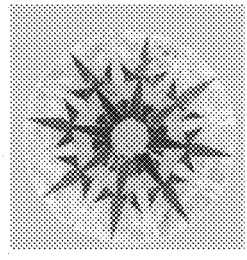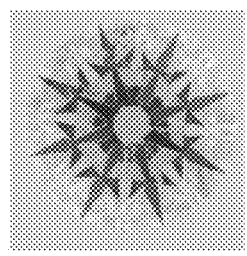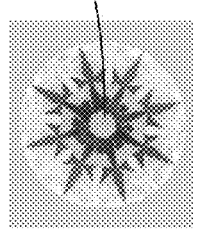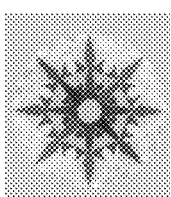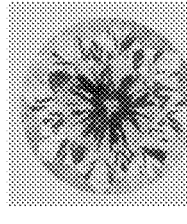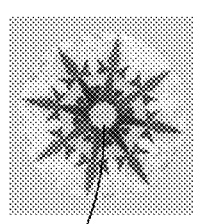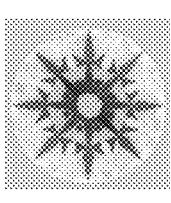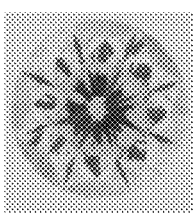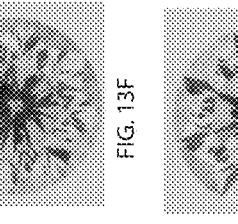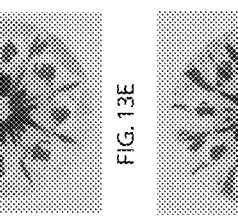
FIG. 13I  FIG. 13J  FIG. 13M  FIG. 13L  FIG. 13K  FIG. 13O  FIG. 13N  FIG. 13A  FIG. 13B  FIG. 13C  FIG. 13D  FIG. 13E  FIG. 13F  FIG. 13G  FIG. 13H

GEM IDENTIFICATION METHOD AND APPARATUS USING DIGITAL IMAGING VIEWER

CROSS REFERENCES TO RELATED APPLICATIONS

This application is a continuation-in-part of U.S. patent application Ser. No. 13/901,445, filed May 23, 2013, and claims the benefit of U.S. Provisional Patent Application Ser. No. 61/695,746, filed Aug. 31, 2012. All of the information disclosed in those applications is hereby incorporated herein by reference in its entirety.

FIELD OF THE INVENTION

This invention relates to the identification of specific gemstones, and in particular to the identification of such gemstones using a digital imaging viewer.

BACKGROUND OF THE INVENTION

As the popularity of owning polished gemstone jewelry has increased dramatically in the second half of the 20th century and since then, the relative importance of a gemstone to the overall net worth of gemstone buying population has increased. In particular, diamonds are no longer just baubles of the rich. As either a discretionary luxury item or an essential engagement ring, the cost of diamonds can be large relative to the household budget of the general population of buyers, but the value, especially the emotional value, can make one particular diamond, to one particular person, virtually priceless beyond monetary value altogether. Any lost or stolen diamond can be replaced quite easily, especially if it was insured by the owner. But, the loss of a diamond imbued with the sentiment of one's marriage commitment, or any one of the other innumerable special remembrances a person may have, is an emotional loss that cannot be filled by a substitute. While other gemstones such as sapphire, ruby, emerald, or tanzanite are not as valuable as diamond, they often hold strong sentimental value to the owner. This makes keeping one's gemstones safely in his or her possession at all times very important to the owner. Not that that would be a bad idea under any circumstance, but it points to two basic underlying facts. First, gemstone owners are just not able to pick their specific gemstone out of crowd of gemstones if they are substantially similar in size. Even if there are only two from which to choose it is very difficult. Second, due to the diamond grading system, diamonds that may appear to be generally similar in appearance, size, and description to the naked eye of a layman can be wildly dissimilar in dollar value. This difference gives a dishonest person motivation to try to switch one diamond for another, an inferior cheap one for a high quality valuable one, because the owner is unlikely to be able to tell the difference.

If gemstone owners could be certain to tell the difference between one gemstone and another, that is, if they could easily identify their own gemstone(s) versus all the others out in the universe, they would not only feel more comfortable wearing them in public and displaying them generally, but also in trusting them to the custody of a third party, such as a jeweler when they need to have their jewelry repaired or reset. Having the ability to identify a gemstone would be valuable to the consuming public just for the benefit of reducing the anxiety they feel about wearing a most prized possession. The idea that if their gemstone were ever lost or stolen, it might be recoverable because it is identifiable, or the notion that an unscrupulous jeweler wouldn't even attempt to deceive them because they would know it instantly, is a real and knowable benefit to the average consumer. Having such ability would also have a real monetary benefit in lower insurance premiums, or even recovery of a lost or stolen item, as well as the protection it would give the owner against being the victim of an outright fraud.

Attempts to create methods of identifying one gemstone from another have been ongoing. At the most advanced level, polished diamonds are sent to grading laboratories where trained technicians, using microscopes and their subjective judgment, based on their training and years of experience, will describe each diamond in terms of a grade on a number of commonly observable characteristics. This is generally referred to as the four Cs grade of the diamond, color, cut, clarity and carat weight. When this analysis includes mapping of the natural flaws in the diamond material itself, that is, when there are observable flaws to be seen, it allows a pretty good method of identifying one diamond from another. However, it is not practical for a consumer to learn or practice diamond grading, it is an expense every time it is performed by the laboratory, and it is time consuming, taking weeks to get results. And of course it requires the owner to let the gem out of his or her possession for all that time, to an extent defeating the entire purpose of having the gem verified in the first place. Moreover, if the diamond has no flaws or only slight flaws, discriminating one versus another of similar grade can be very difficult.

The other most common approach to doing field identification of diamonds is to simply mark them in such a way as to be unique, such as with a readable serial number or a symbol. There are at least two common methods of accomplishing this marking: laser engraving the girdle, that is, the equator or waist line of the diamond, and plasma etching or engraving a surface, most commonly the table surface or top usually flat facet of the diamond. Both of these methods have certain practical flaws.

With laser engraving the inscription is very small, requiring magnification to be visible. The printing itself is a very crude burning process which is difficult to read. Further, it is quite easy and inexpensive to remove a laser mark and to produce another mark of the same exact type. This means swapping a diamond with a laser engraved serial number on it is no substantial barrier. Additionally, once the diamond is mounted in a ring or jewelry, the mounting prongs will many times block the inscription from view, so even if a consumer were are able to magnify the image large enough to read, which is not particularly easy, the consumer still may not be able to see it.

The other alternative, plasma etching or engraving of the table, results in a marking that is also not easily readable without significant magnification. Although special inexpensive inscription viewers have been developed for consumers, such a viewer may not always be on the person when the person may be desire to use it. And though the inscription is not easily removed, and it is not easily duplicated (it is often impossible to duplicate), it is still not widely adopted by the jewelry industry. This can be because of a number of factors, including that it is a new technology, that it is relatively costly to apply in small quantities, and that it is not widely available as it requires very expensive high-technology equipment and skilled technicians. There is also an industry bias, and from there a consumer bias, against the idea of etching the top surface of a diamond, because of the perception that it could harm the value of the diamond. This bias can usually be overcome by educating consumers about the benign nature of this technique.

U.S. Pat. Nos. 7,468,786 and 8,035,807, which are incorporated by reference herein in their entirety, and invented by the same inventors as the present invention and owned by the same assignee, disclose a less expensive and more effective viewer (referred to hereinafter as an Engraved Gemstone Viewer) using the concept of illuminating the surface of the polished diamond in such a way as to create a spectral light reflection much like that of a mirror. The Engraved Gemstone Viewer is effective but lacks the convenience of being with the person at all times that engraving might be needed to be viewed, and further, lacks a way to memorize the image for later recall, comparison analysis, or remote communication of the information contained in the image.

Thus, there is a need for a gemstone identification system that is accurate over 90% of the time; is easy to use by the general public without special skills or training; is deployable on short time notice and produces results quickly; has a method of recording data for later recall and communication to third parties, such as the police; does not change or alter the gemstone in a detrimental way; is not be easily defeated or susceptible to fraud; is conveniently and widely available to consumers; and is inexpensive.

SUMMARY OF THE INVENTION

The present invention is a system for positively identifying a light colored polished gemstone, comprising an appliance designed for use with an electronic communication device with a digital imaging camera (for example, a smart phone, tablet computer or any other camera/internet capable device) and software running on the communications device facilitating image data capture and thereafter processing the data into comparative criteria and comparing the data of the subject gemstone against a database of collected data to match the gemstone data to a gemstone data file residing in the database. The system may include transmission of the data to operating servers for analysis, or conducting the analysis locally on the communications device.

An integral part of the system is the appliance designed to work with the electronic communication device. The appliance is a gemstone viewer that is easily attached to and removed from the electronic communication device, thereby allowing the device's camera and its inherent digital imaging functionality to capture a digital image of a gemstone that is magnified by a lens of the gemstone viewer, and oriented such that the gemstone facets reflect the light and dark surfaces of the gemstone viewer body, thereby creating a two dimensional image accentuating the cut facet surfaces and features of the gemstone.

It will be understood by those skilled in the art that one or more aspects of this invention can meet certain objectives, while one or more other aspects can lead to certain other objectives. Other objects, features, benefits and advantages of the present invention will be apparent in this summary and descriptions of the disclosed embodiment, and will be readily apparent to those skilled in the art. Such objects, features, benefits and advantages will be apparent from the above as taken in conjunction with the accompanying figures and all reasonable inferences to be drawn therefrom.

BRIEF DESCRIPTION OF THE DRAWINGS

FIG. 4 is an enlarged top plan view of the gemstone viewer shown in FIG. 1.

FIG. 5 is a side sectional view of the gemstone viewer shown in FIG. 4, taken along line 5-5 of FIG. 4.

FIG. 13 is a group of example images of diamonds showing some that match and some that do not match.

DESCRIPTION OF THE INVENTION

Figure 1:
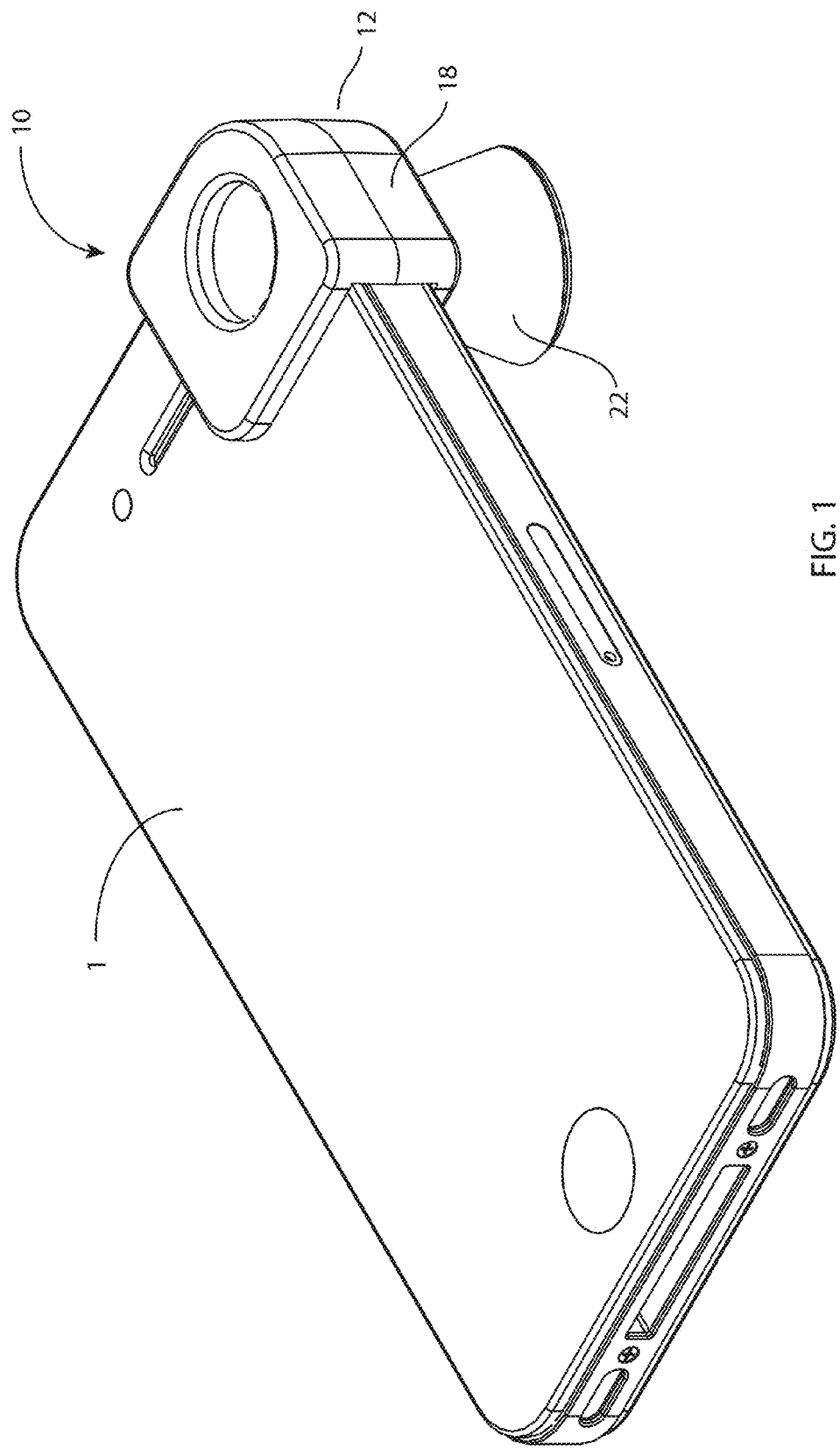
FIG. 1 is a perspective top-side view of a gemstone viewer for use in the present invention, shown mounted on an electronic communication device having a camera.
Figure 2:
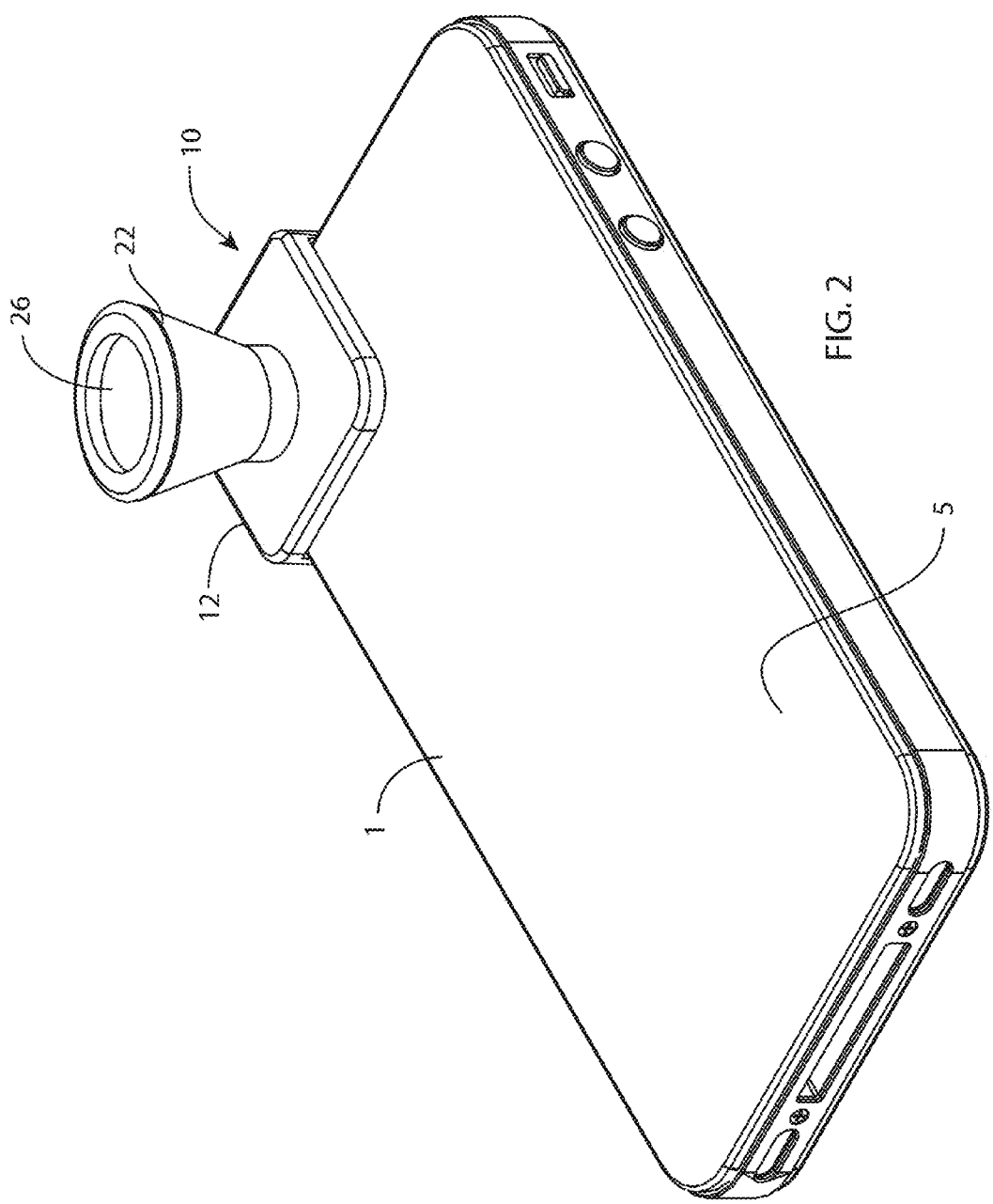
FIG. 2 is a perspective bottom-side view of the gemstone viewer shown in FIG. 1.
Figure 3:
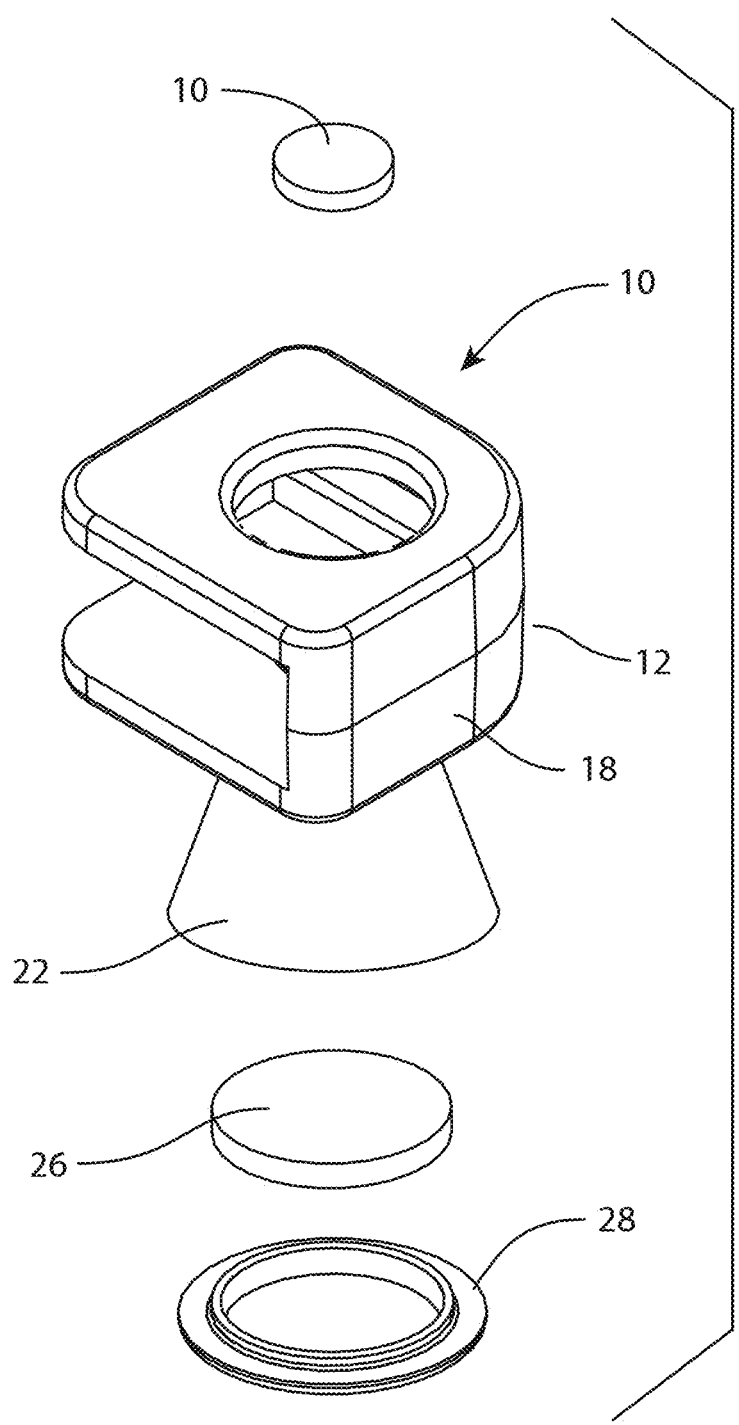
FIG. 3 is an exploded perspective view of the gemstone viewer shown in FIG. 1.
Figure 7:
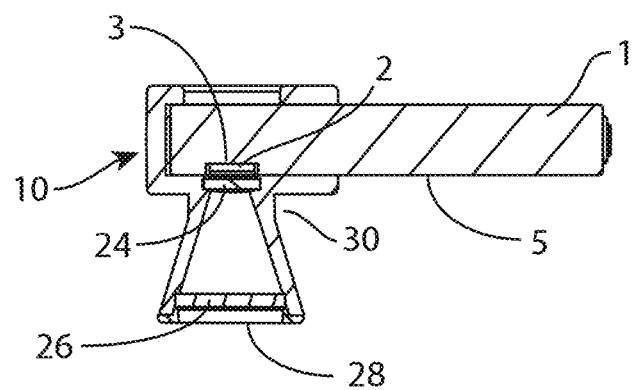
FIG. 7 is a side sectional view of the gemstone viewer of FIG. 6, taken along line 7-7 of FIG. 6.
Figure 6:
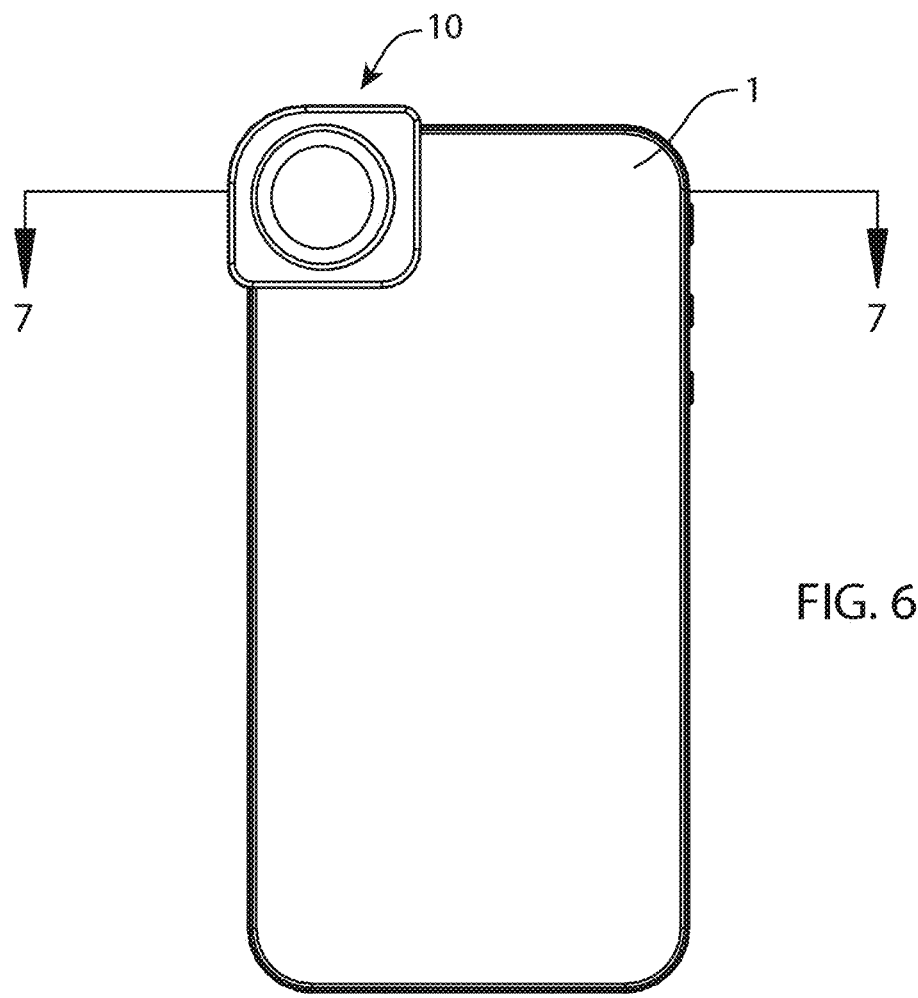
FIG. 6 is a bottom plan view of the of the gemstone viewer shown in FIG. 1.
Figure 8:
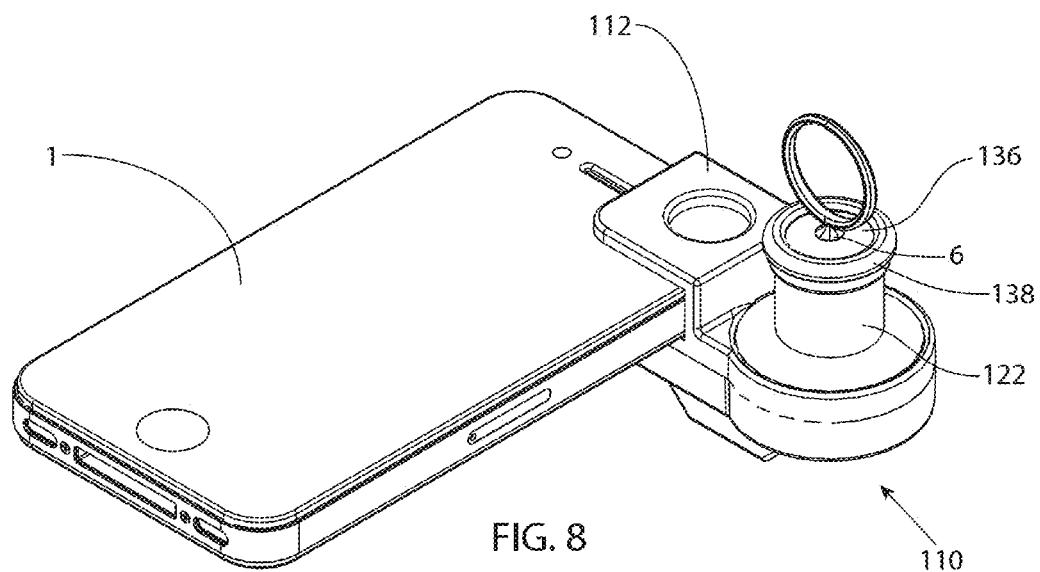
FIG. 8 is a perspective top-side view showing another embodiment of a gemstone viewer in accordance with the invention showing a gemstone mounted on a ring and in position for imaging.
Figure 8A:
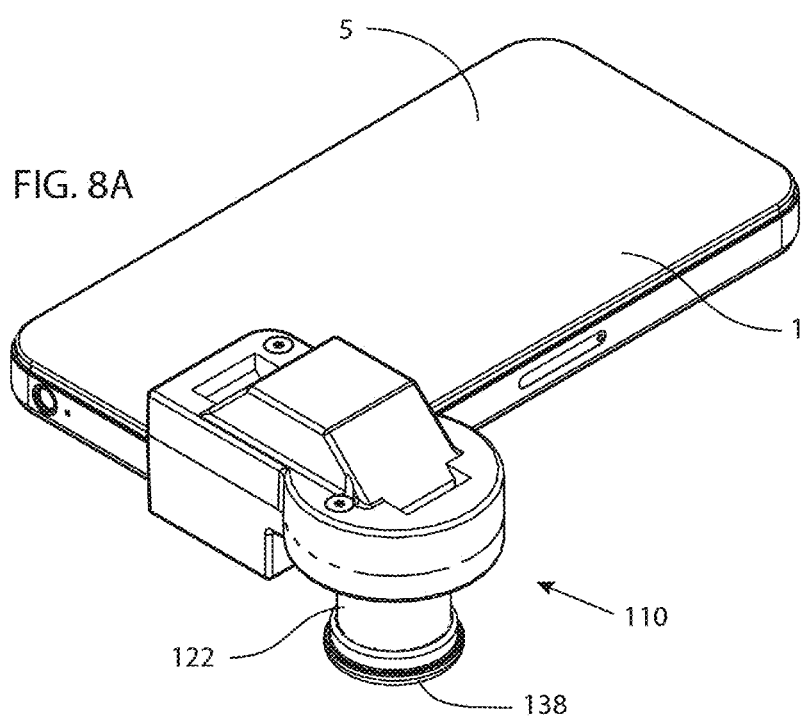
FIG. 8A is a perspective bottom-side view of the apparatus shown in FIG. 8.
Figure 10:
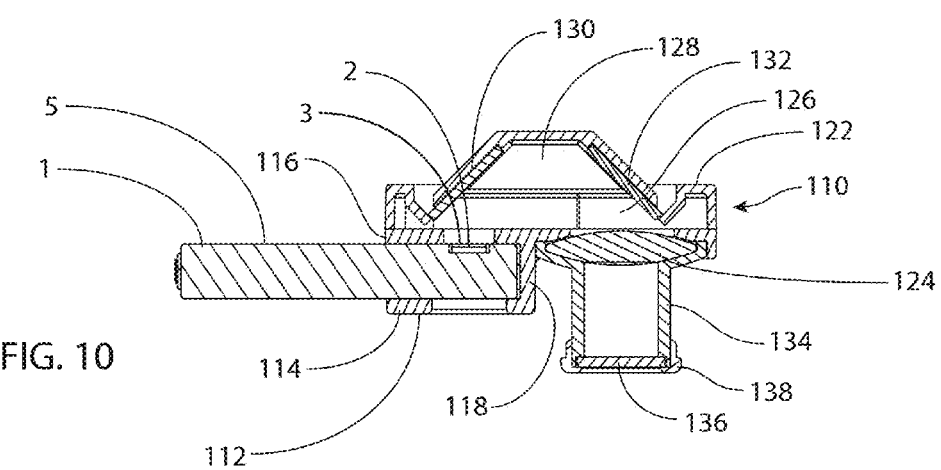
FIG. 10 is a sectional view of the apparatus shown in FIG. 9, taken along line 10-10 of FIG. 9.
Figure 9:
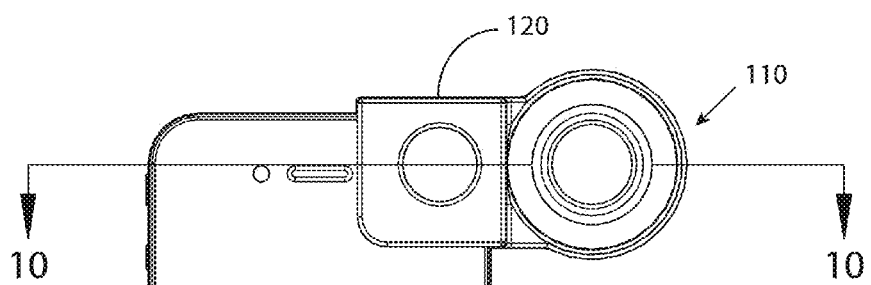
FIG. 9 is a top view of the apparatus shown in FIG. 8.
Figure 9A:
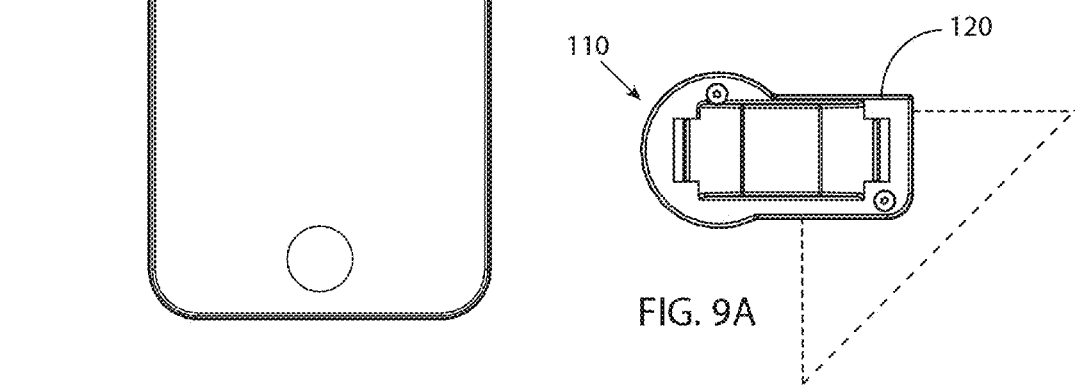
FIG. 9A is a bottom view of the apparatus shown in FIG. 8.
Figure 11:
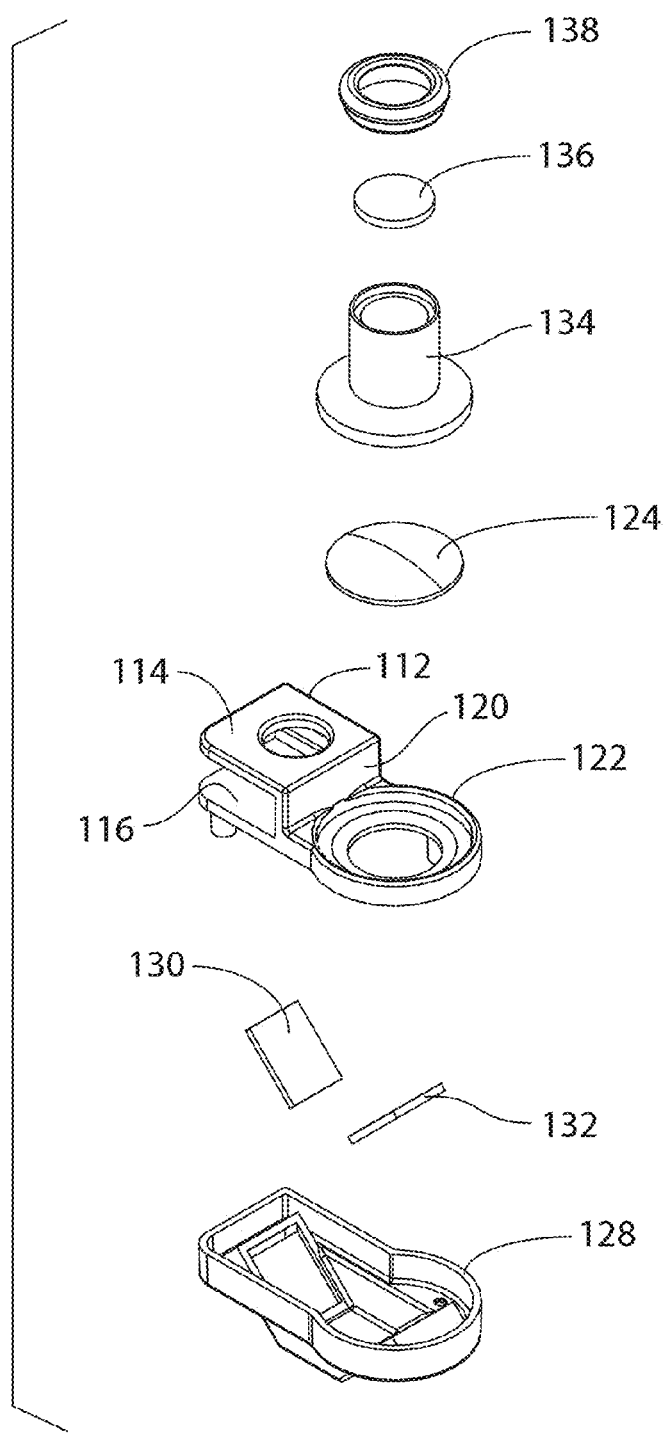
FIG. 11 is an exploded view of the apparatus shown in FIG. 10.

As indicated, the present invention pertains to a system for positively identifying a polished light colored gemstone. Such light colored gemstones that may be identified using the present invention include but are not limited to diamond, sapphire, ruby, emerald, and tanzanite. The invention includes an appliance designed for use with an existing electronic communication device with a digital imaging camera, for example, a tablet computer, smartphone, or any other camera/internet capable device. The invention further includes software running on the communications device that facilitates image data capture of a gemstone. Thereafter, the data captured about the subject gemstone is processed through comparative criteria and compared against previously collected data, to determine whether the newly taken data matches the previously collected data. The previously collected data may be residing in a database. Additionally, the system may include transmission of the data to remote servers for analysis, or the analysis may be conducted locally on the electronic communication device.

As described earlier, an integral part of the system is the appliance designed to work with the electronic communication device. The appliance is further described as a gemstone viewer that allows the communication device's imaging camera, and its inherent digital imaging functionality, to capture a digital image of a gemstone. The appliance includes a lens that may magnify the gemstone. The appliance further includes a focusing plane that positions the gemstone such that the gemstone facets reflect the light and dark surfaces of the gemstone viewer body. The reflections are sensed by the imaging camera thereby creating a two dimensional image accentuating the cut facet surfaces and features of the gemstone.

One embodiment of a gemstone viewer 10 in accordance with the invention is shown in FIGS. 1-7. The gemstone viewer 10 is removably attached to an electronic communication device 1 that includes a camera lens 2. In the embodiment shown, the electronic communication device 1 is an Apple® iPhone®, but any suitable device may be used without departing from the invention including for example, an iPad® or other tablet computer, or a laptop or desktop computer having a camera attached.

In the embodiment shown, the viewer 10 has a base 12 (shown generally square in shape in the embodiment shown although many other shapes would function equally well) to receive the corner of the electronic communication device 1 where the camera lens 2 and camera 3 is positioned on the back side 5 of the electronic communication device. Alternative embodiments of the gemstone viewer may also be attached to the electronic communication device to use a front facing camera, if available. As shown, the base 12 has a top plane 14 and bottom plane 16 spaced apart by two adjoining side planes 18, 20, which most preferably is formed unitarily but may be formed of parts and assembled as well. The base 12 is open on the opposing two adjoining sides so as to accommodate the thickness of the personal communications device 1 that is received through the two open sides. The top, bottom and two side planes 14, 16, 18, 20 of the base 12 are precisely spaced to make frictional contact with the personal communications device 1 so as to secure the viewer 10 to the personal communications device without applying additional pressure or mechanical means. In alternative embodiments of the viewer 10, the base 12 may have a different shape and size so as to correctly orient the viewer to receive a different model of smartphone or personal communications device, with the camera lens in a different position.

A viewer body 22, shown as a funnel shape in this embodiment, is attached to or formed integrally with the bottom plane 16. The viewer body 22 encloses a lens 24 at the level of the bottom plane 16 that is coaxially aligned with but not contacting the camera lens 2 of the electronic communication device 1. The bottom plane 16 is open to allow an unobstructed path for light to pass through the lens 24 to the camera lens 2. In the embodiment shown, the lens 24 visually enlarges objects in the view of the camera beyond that which is otherwise possible by the unaided camera lens 2. Additionally, the lens 24 allows the camera lens 2 to focus on the gemstone, which may be closer to the camera lens 2 than the minimum focusing distance of the camera lens. In the embodiment shown, the lens 24 magnifies the gemstone preferably at least 10×, but greater or lesser magnifications may also be used without departing from the invention as long as the software can process unique identifying characteristics of the gemstone. For example, advancements in digital camera sensors may make it possible for the lens 24 to minimally magnify the gemstone, if at all, but still have enough detail in the image to be able to perform the identification analysis. As such, the lens 24 may merely allow the camera lens 2 to focus on the gemstone, but not provide any magnification.

As shown, the viewer body 22 protrudes generally perpendicularly away from the bottom plane 16. The opposite end of the viewer body 22 terminates at a plane where a focusing glass 26 is held in place by a retaining ring 28. The focusing glass 26 and the lens 24 are held at the correct distance from each other by the viewer body 22 such that the camera lens 2 is properly focused through the lens at the top of the viewer body to the surface of a gemstone 6, placed against the outside surface of the focusing glass. The viewer body 22 is made of any suitable translucent material that allows diffuse ambient light to illuminate a gemstone placed on the focusing glass 26.

FIGS. 8-11 show another embodiment of a gemstone viewer in accordance with the invention. In this embodiment, the smartphone viewer 110 has a base 112 to receive the corner of the electronic communication device 1 where the camera lens 2 is positioned on the back side 5 of the electronic communication device. The base 112 has a top plane 114 and bottom plane 116 spaced apart by two adjoining vertical side planes 118, 120 and is open on the opposing two adjoining sides so as to accommodate the thickness of the electronic communication device 1 that is received through the two open sides. The top plane 114, bottom plane 116 and two side planes 118, 120 of the base 112 are precisely spaced to make contact with the electronic communication device 1 so as to secure the base to the electronic communication device primarily by friction without applying additional pressure or mechanical means. In alternative embodiments of the device the base may be a different shape and size so as to correctly orient the device to receive any particular electronic communication device that includes an imaging camera.

In the embodiment shown, a viewer body 122 is attached to the bottom plane 116. The viewer body 122 is a structure sized and positioned to accommodate a lens 124 generally at the level of the bottom plane 116 of the base 112 but offset from the camera lens 2 of the electronic communication device. The bottom plane 116 includes an opening 126 to allow an unobstructed path for light to pass through to a channel body 128 of the viewer 110. The channel body 128 includes a first 45° mirror 130, and a second 45° mirror 132. Mirrors 130, 132 direct light that has passed through a focusing tube 134 and the lens 124. In the embodiment shown, the lens 124 is of such a calibration as to visually enlarge objects in the view of the camera lens 2 ten times beyond that which is otherwise possible by the unaided camera lens itself. As discussed above, in this embodiment, the lens 124 also may magnify the object in view of the camera any suitable amount without departing from the invention. The viewer body channel 128 extends laterally to the edge of the base bottom plane 116, where the lens 124 is positioned. The focusing tube 134 is positioned upon the lens 124 and terminates at the plane of a focusing glass 136, which is held in place by a retaining ring 138. The focusing glass 136 is positioned to receive a gemstone 6, table face down on the focusing glass when the electronic communication device 1 is held with its display screen horizontally flat (as if flat on its back on a table). The focusing glass 136 and lens 124 are held at the correct distance from each other by the viewer body 122 such that the camera lens 2 is properly focused through the two 45° mirrors 130, 132 and the lens to the surface of a diamond 6 placed against the surface of the focusing glass. The portion of viewer body 122 between (in terms of the line of sight) the lens 124 and the camera 3 blocks ambient light from directly striking the gemstone when placed in contact with the focusing glass 136.

The viewer body 122 is constructed of an opaque material that is either dark in color or coated black. The focusing tube 134 is translucent so as to allow transmission of diffuse light into the tube. The geometry of the focusing tube 134 is constructed in order that the properties of the light illuminating the diamond are consistent and repeatable.

In use, the image of the known gemstone as created by the gemstone viewer is captured by the camera 3 of the electronic communication device 1 and stored in memory using software on the device. Of course, the image of the known gemstone may be generated at any time, and may even be made with other equipment by the manufacturer or jeweler, for example. In such an instance, the equipment used to create the image of the known gemstone must have the same geometric and material properties of the gemstone viewer 10, 110. Because trust is such a critical component between a jeweler and the customer, the customer may prefer to create the image of the known gemstone despite the presence of an image created by the manufacturer or jeweler.

Turning now to FIG. 16, a "server" embodiment of the present invention is shown. A user 200 creates a reference image 300 of a gemstone 6 by placing the gemstone on the gemstone viewer 110, which is removably attached to the electronic communication device 1. The reference image 300 may then be uploaded and stored, such as via an internet connection native in the electronic communication device or any other suitable means, to software running on a remote server, where the reference image is entered as part of a permanent archival database 302 and registry. Alternatively, in a "local" embodiment of the present invention the reference image 300 is simply stored in a memory on the electronic communication device 1, whether or not in a database, as the reference image of the gemstone 6. The reference image 300 may then be processed so as to measure and calibrate the unique identification characteristics of the reference image, and there may be created and assigned a cataloging serial number to be used in rapid retrieval and comparison analysis. Once the reference image 300 is thus obtained, the user 200 may later compare a gemstone 6 he has, for instance, received back from a jeweler, to determine if it is the same gemstone as was originally turned over to the jeweler. The user 300 again uses the gemstone viewer 110 in conjunction with the electronic communication device 1 to make a comparison image 350 of the gemstone he is now holding. The comparison image 350 is then analyzed by the software, whether the software on the server in the server embodiment or the app on the electronic communication device 1 in the local embodiment, and compared to the reference image 300 of the original gemstone 6.

According to the invention, the user 200 may be able to retrieve any gemstone image from the electronic communication device memory for later viewing. The user may also request the assigned catalog serial number to be downloaded from a server database.

In a preferred embodiment, when the need arises for the user to verify that a particular gemstone (the "comparison gemstone," which he has in hand) is in fact the same gemstone as he had previously obtained, the user will open the app on the electronic communication device 1 and select "compare gemstones" or a similar option. The app will then instruct the user as to the steps to follow to make a comparison to the existing archived images. The user will proceed to record a comparison image 350 of the comparison gemstone using the same steps as with the original gemstone previously obtained.

In one embodiment of the invention, the software present on the electronic communication device instructs the user 200 when the gemstone 6 is in the proper position on the gemstone viewer. This allows the gemstone viewer to accommodate a variety of gemstone shapes and sizes. For example, the software may display a live view of the camera sensor with a target or similar image overlaid on the camera view. Then, when the user places a gemstone on the focusing glass, he or she can use the target to align the gemstone. The software may also indicate to the user when the gemstone is in the proper position with an audible or visual clue. Additionally, the software may automatically capture an image upon proper positioning of the gemstone.

In the server embodiment, upon uploading the comparison image 350 to the server, the server software 304 will analyze the comparison image, and calibrate the unique identification characteristics for that gemstone, and compare the calibrated data from the comparison image 350 to the reference image 300 to determine if the images were taken of the same gemstone, or from two different gemstones. The server software will then send a notification 306 to the electronic communication device 1 advising the user 200 if the images are of the same gemstone, or of different gemstones, and/or advise the user of the likelihood or probability that the gemstones are one and the same.

In the local embodiment, upon obtaining the second image, the software onboard the electronic communication device 1 will analyze the comparison image 350, and calibrate the unique identification characteristics for that gemstone, and compare the calibrated data from the comparison images and the reference image 300 to determine if the images were taken of the same gemstone, or from two different gemstones. The software on the electronic communication device 1 will then advise the user 200 if the images belong the same gemstone, or from different gemstones, and/or advise the user of the likelihood or probability that the gemstones are one and the same. The user is then able to make an informed decision about the gemstone in hand as being the one anticipated, or a substituted gemstone.

This system is may also be useful to law enforcement personnel, who could use the gemstone viewer, software, and server on any gemstone that has been recovered from loss or theft, especially in connection with the server embodiment. As long as the gemstone in question has been previously registered with the server, law enforcement personnel can locate a match in the server database, and thereby have identified for them the owner of the gemstone.

The software for use in connection with the imaging aspect of the invention employs pattern matching. In general, pattern matching is well known, but the application of pattern matching here is specific and novel. In particular, the pattern matching here looks for inclusions or impurities in the gemstone, as well as the particular dimensions of the facets of the gemstone, which are unique for each gemstone because they are hand cut. Additional optical characteristics of the gemstone, such as color and luminance, may also be measured and stored in the database. In the server embodiment, some of the pattern matching functionality is in the software on the electronic communication device, and some of the functionality is in the server software. Of course, some or all of the pattern matching functionality may be performed by software in either the electronic communication device or in a remote device or server. For example, the server may merely act as a repository of images, with all of the processing done by the software on the electronic communication device. As indicated above, in the local embodiment, even the store of images is entirely in the storage of the electronic communication device, and accessible by the app, even if no internet connection is available.

Figure 12:
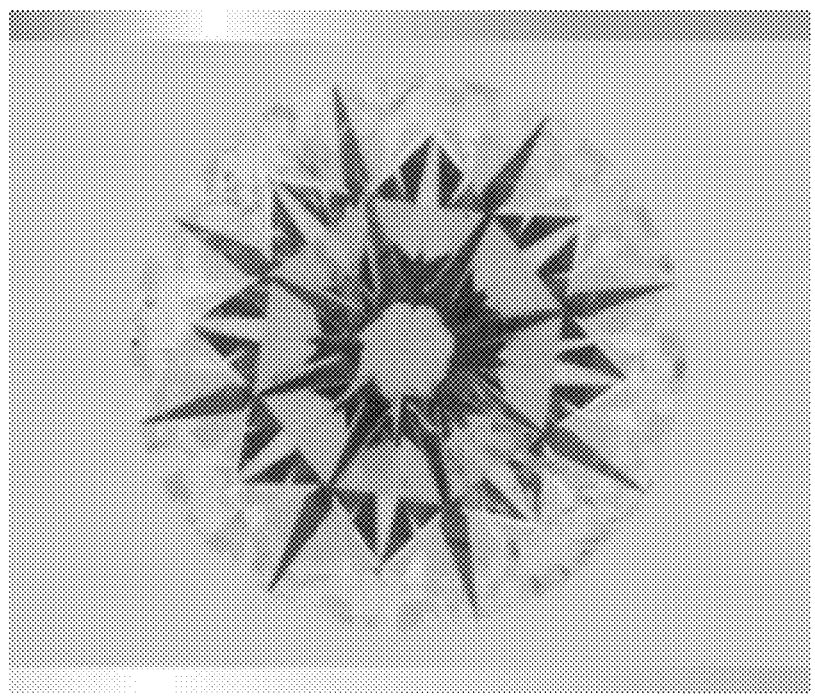
FIG. 12 is an image of a diamond created according to one aspect of the invention.
Figure 14:
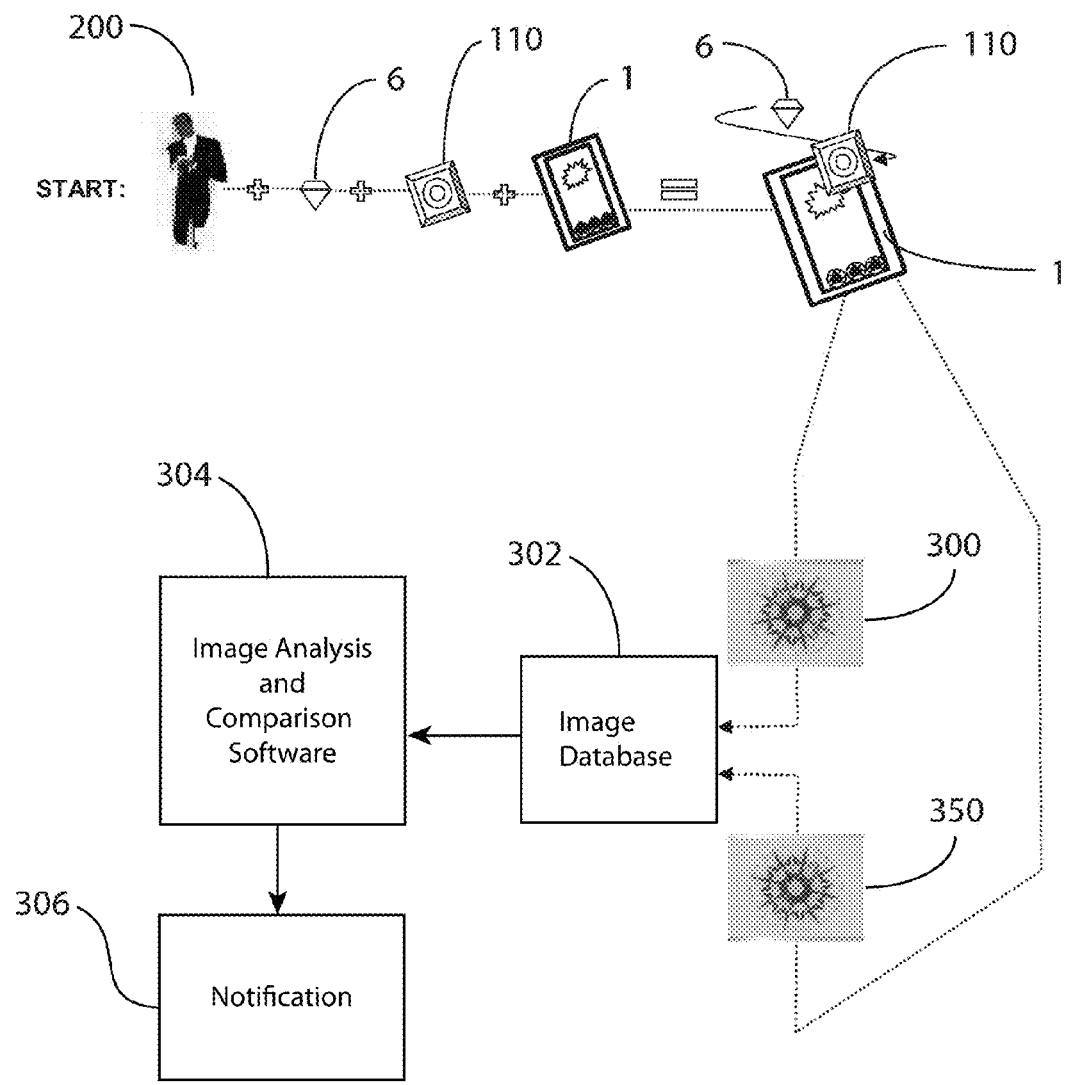
FIG. 14 is a flow chart showing the logical flow of one aspect of the invention.

In operation, as described above, as shown in FIGS. 12-14, the system begins with taking an image of the known gemstone, to be used for later comparison. Using the electronic communication device and the viewer 10, 110 according to the present invention, an image similar to that shown in FIG. 12 is taken, broken down into pixels, and the data of those pixels stored for later comparison. Then, when it comes time to determine whether the comparison gemstone is the same gemstone as the original, an image is taken of the comparison gemstone. That image is broken down into pixels and a data file is created therefrom.

First, a preliminary or gross comparison is conducted. Gross items such as the size and shape of the stone, the size and shape of the center of the stone, and the number, size and shape of any inclusions or imperfections, are compared. If any of the gross parameters is different, then it is immediately clear that the comparison gem is not the original gem. If all of the gross parameters are the same, then a pixel by pixel pattern matching is conducted. In the most preferred embodiment, the two images are overlaid with respect to each other, and rotated through a series of angles with respect to each other. The relative angle that produces the greatest number of pixel matches is settled upon. Once the relative angle is settled upon, then the percentage of the pixels that do match is calculated, and the result is produced. For example, the result might be that there is an 89% pixel match, or that, given the number of pixels that match, there is a 93% chance that the original gem and the comparison gem are one and the same.

FIG. 13 is a group of images included for the purpose of showing examples of sets of images that match and sets that do not match. As shown, the non-matching pairs are 13A/B, 13C/D, 13E/F, and 13G/H. The matching sets are 13I/J, 13K/L/M, and 13G/H. To the naked eye, it is difficult to spot differences between sets 13A/B and 13C/D. However, using the image comparison algorithm described herein, the software is able to distinguish between very similar gemstones. For example, at first glance, FIGS. 13A and 13B appear nearly identical. A close examination of the center of the stone shown in FIG. 13A reveals that it has a well-defined octagonal center 40, whereas the center 42 of FIG. 13B is not nearly as well-defined. FIGS. 13I/J show the same stone. The stone shown in FIGS. 13I/J include a distinct pattern of inclusions 50. In FIG. 13I, the inclusions are visible at the 9 o'clock position. In FIG. 13J, the same inclusions 50 are visible at the 11 o'clock position. The software is capable of recognizing the identical pattern, even though the gemstones are not in the same orientation. Experience over time will determine what percentage of similarity or probability, and what gray scale level and resolution, and similar parameters, are necessary, to reliably determine whether the original gem and the comparison gem are the same gem.

While this invention is susceptible of embodiment in many different forms, the drawings show and the specification describes one of the preferred embodiments of the invention. It should be understood that the drawings and specification are to be considered an exemplification of the principles of the invention. They are not intended to limit the broad aspects of the invention to the embodiments illustrated.

What is claimed is:

1. A system for positively identifying a gemstone using an electronic communication device having a camera, the system comprising:
a gemstone viewer removably attached to the electronic communication device;
the gemstone viewer having a bottom plane and a viewer body coaxially aligned with the camera and extending from the bottom plane and terminating at a focusing plane;
a focusing glass attached to the viewer body at the focusing plane; and
a software application running on the electronic communication device facilitating capture of image data regarding the gemstone and thereafter processing the image data into comparative criteria and comparing the data of the gemstone against a database of previously collected data to determine whether a match exists between the image data and a gemstone data file residing in the database.

2. The system of claim 1, wherein the viewer body is made of translucent material that causes diffuse ambient light to illuminate the gemstone when it is placed on the focusing glass.

3. A gemstone viewer for working with an electronic communication device having a camera lens, the gemstone viewer comprising:
a base, including a top plane and bottom plane spaced apart from each other by one or more adjoining side planes;
a viewer body, associated with the base;
a viewer lens connected to the viewer body; and
a focusing glass connected to the viewer body, with the viewer lens positioned between the focusing glass and the camera lens, based on a line of sight;
the focusing glass and the viewer lens being held at a sufficient distance from each other by the viewer body such that the camera lens is properly focused through the viewer lens to the surface of a gemstone when the surface of the gemstone is placed against the focusing glass.

4. The gemstone viewer of claim 3, wherein the viewer lens is connected to the viewer body generally coaxially aligned with but not contacting the camera lens.

5. The gemstone viewer of claim 3, wherein the top plane, bottom plane and one or more side planes arranged to make contact with the electronic communication device so as to removably secure the base to the electronic communication device primarily by friction and without applying additional pressure or mechanical means.

* * * * *